United States Patent
Landon

(10) Patent No.: US 10,034,756 B2
(45) Date of Patent: Jul. 31, 2018

(54) ORTHOPAEDIC IMPLANTS AND METHODS

(75) Inventor: Ryan Lloyd Landon, Southaven, MS (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 13/209,997

(22) Filed: Aug. 15, 2011

(65) Prior Publication Data

US 2012/0041564 A1 Feb. 16, 2012

Related U.S. Application Data

(60) Provisional application No. 61/373,606, filed on Aug. 13, 2010, provisional application No. 61/373,783, filed on Aug. 13, 2010.

(51) Int. Cl.
*A61F 2/38* (2006.01)
*A61F 2/30* (2006.01)

(52) U.S. Cl.
CPC .......... *A61F 2/389* (2013.01); *A61F 2/30734* (2013.01); *A61F 2/30767* (2013.01); *A61F 2002/3092* (2013.01); *A61F 2002/30331* (2013.01); *A61F 2002/30332* (2013.01); *A61F 2002/30354* (2013.01); *A61F 2002/30405* (2013.01); *A61F 2002/30769* (2013.01); *A61F 2002/30845* (2013.01); *A61F 2002/30878* (2013.01); *A61F 2002/30884* (2013.01); *A61F 2002/30899* (2013.01)

(58) Field of Classification Search
USPC .......................................... 623/20.32, 20.34
See application file for complete search history.

(56) References Cited

U.S. PATENT DOCUMENTS

| | | | |
|---|---|---|---|
| 5,074,880 A | * | 12/1991 | Mansat ...................... 623/20.32 |
| 5,336,266 A | | 8/1994 | Caspari et al. |
| 5,609,641 A | | 3/1997 | Johnson et al. |
| 5,824,103 A | * | 10/1998 | Williams ................... 623/20.32 |

(Continued)

FOREIGN PATENT DOCUMENTS

| | | | | |
|---|---|---|---|---|
| EP | 1792585 A3 | 8/2007 | | |
| GB | 2463066 A | * | 3/2010 | ............... A61F 2/34 |
| JP | 2001087292 A | 4/2001 | | |

OTHER PUBLICATIONS

International Search Report and Written Opinion for International Application No. PCT/US2011/047513, dated Mar. 15, 2012.

(Continued)

*Primary Examiner* — David Isabella
*Assistant Examiner* — Christine Nelson
(74) *Attorney, Agent, or Firm* — Taft Stettinius & Hollister LLP

(57) ABSTRACT

There is provided a tibial component comprising: a tibial tray with an inferior side; and a support member connected to the inferior side of the tibial tray, the support member having a stem portion, the support member further comprising at least one opening. In one embodiment, the at least one opening is constructed and arranged to receive a sawblade or an osteotome. In another embodiment, the at least one opening is comprised of solid material but is radio-lucent. In yet another embodiment, the at least one opening is comprised of solid material and is frangible.

11 Claims, 16 Drawing Sheets

(56) References Cited

U.S. PATENT DOCUMENTS

| | | | |
|---|---|---|---|
| 6,379,386 B1* | 4/2002 | Resch | A61B 17/1604 623/19.13 |
| 2003/0028254 A1 | 2/2003 | Hunter et al. | |
| 2006/0015101 A1 | 1/2006 | Warburton et al. | |
| 2006/0142869 A1* | 6/2006 | Gross | 623/20.34 |
| 2007/0129808 A1* | 6/2007 | Justin et al. | 623/20.15 |
| 2009/0228114 A1* | 9/2009 | Clark et al. | 623/20.36 |
| 2011/0270404 A1* | 11/2011 | Khan et al. | 623/22.32 |

OTHER PUBLICATIONS

English Translation of Japanese Reference 2001-87292, published Apr. 3, 2001.

* cited by examiner

ORTHOPAEDIC IMPLANTS AND METHODS

CROSS-REFERENCE TO RELATED APPLICATIONS

This application claims the benefit of U.S. Provisional Application No. 61/373,606, filed 13 Aug. 2010 and U.S. Provisional Application No. 61/373,783, filed 13 Aug. 2010. The disclosure of each prior application is incorporated by reference in its entirety.

RELATED FIELDS

Orthopaedic implants and methods involving the same, such as, but not limited to, orthopaedic implants and methods for the proximal tibia, such as tibial trays that may include one or more of a keel and/or a stem and methods for revising the same.

BACKGROUND

There are several factors that are potentially relevant to the design and performance of orthopaedic implants. In the example of a tibial tray, a non-exhaustive list of such factors includes the implant's flexibility (or the flexibility of certain portions of the implant or its flexibility about certain axes or other constructs), which may indicate the degree to which the tray will conform to the potentially uneven resected surfaces of a proximal tibia; the implant's rigidity (or the rigidity of certain portions of the implant or its rigidity about certain axes or other constructs), which may indicate the degree to which stresses or other forces imposed by the bony and other anatomy associated with the knee joint will be transmitted to the peripheral hard cortical shell of the proximal tibia; the implant's resistance to rotation; the amount of bone preserved; and/or other potentially relevant factors. In some instances, accommodation of these or other factors may require trade-offs to balance competing factors. In some instances, one or more of these factors will not be considered or given a high level of importance to the design of an orthopaedic implant.

Some known tibial trays include a fin or a keel that may increase the strength of the implant while also helping to prevent rotation relative to the bone. In some instances, such fins or keels may present certain drawbacks. For instance, in some cases, the fin or keel may impede the visualization of the implant and surrounding anatomy using x-ray or other imaging technologies. For instance, it may be desirable in some cases to visualize the implant and its surrounding anatomy, including the surrounding bony anatomy, by taking one or more x-rays in planes such as coronal and sagittal planes or in other planes to assess whether the implant may be loosening over time. Such loosening might be indicated by lucent lines appearing in the x-ray image around portions of the implant or other indications that the bone has receded from the implant or otherwise has become loose. In some instances, a fin or keel of the implant may obstruct the ability to view such lucent lines or may otherwise hinder the evaluation of the image. Other orthopaedic components might feature these or other structures similarly impairing visualization of the implant in the bone and other anatomy.

Some known tibial trays are difficult to remove or revise. For some revision procedures, it is necessary to cut around the existing implant or otherwise position instrumentation about the implant to loosen it from the surrounding bone and/or other anatomy before removal. In some instances, particularly, for instance, some instances where the implant is a tibial tray having a keel, it may be difficult to cut around certain portions of the keel or otherwise access certain areas of the bone-implant interface to loosen the implant. It may be particularly difficult, for instance, to access certain areas of the bone-implant interface depending on the surgical approach taken. For instance, if an anterior-medial incision is used to access the knee joint, the keel structure may impede a surgeon's access to posterior-lateral portions of the bone-implant interface. In such instances, removal of the implant may undesirably require excessive or unintended bone removal as well.

In some instances, stability or fixation of the implant, such as a tibial tray or other implant, in the bone may be of some significance. For instance, the distribution of "hard" versus "soft" bone is not always uniform or predictable, and, in some instances, during bone preparation a punch, drill or other instrument may penetrate the bone at an undesired angle or position since it may tend to follow the path of least resistance into softer bone. Moreover, in some instances, such as some tibial cases, distal metaphyseal bone may tend to be spongier and softer than proximal metaphyseal bone. In some implant cases, it may be difficult to achieve adequate fixation or other stability in the distal metaphyseal bone. Moreover, with some implants, including some tibial implants, there may be a tendency over time for the implant to subside or migrate.

SUMMARY

There is provided a tibial component comprising: a tibial tray with a superior side and an inferior side; and a support member connected to the inferior side of the tibial tray, the support member having a stem portion, the support member further comprising at least one opening. In one embodiment, the stem portion slants at an angle relative to the inferior surface. In another embodiment, the stem portion has a proximal end and a distal end, and the proximal end is connected to the inferior side of the tibial tray. In yet another embodiment, the tibial tray and the support member are monolithic. In one particular embodiment, the tibial tray and the support member have a male/female arrangement. In another embodiment, the tibial component further comprises a porous bead coating. In still another embodiment, the at least one opening is constructed and arranged to receive a sawblade or an osteotome. In one embodiment, the at least one opening is comprised of solid material but is radiolucent. In yet another embodiment, the at least one opening is comprised of solid material and is frangible. In another embodiment, the tibial component further comprises a modular stem removably attached to the stem portion. In one embodiment, the support member includes at least two arms, and each of said arms defines an opening. In another embodiment, the at least two arms are angled relative to one another.

Some of the non-limiting embodiments of tibial trays described herein include one or more fins or keels that include or define holes, openings, recesses, areas formed or filled with different materials, or other structures or features. Some of the non-limiting embodiments of tibial trays described herein may additionally or alternatively include a monolithic, modular or otherwise connected fluted stem. The present application is not limited to tibial trays; however, and one of skill in the art will recognize that at least some of the concepts presented herein could be applied to other orthopaedic implants.

DETAILED DESCRIPTION

Figure 1:
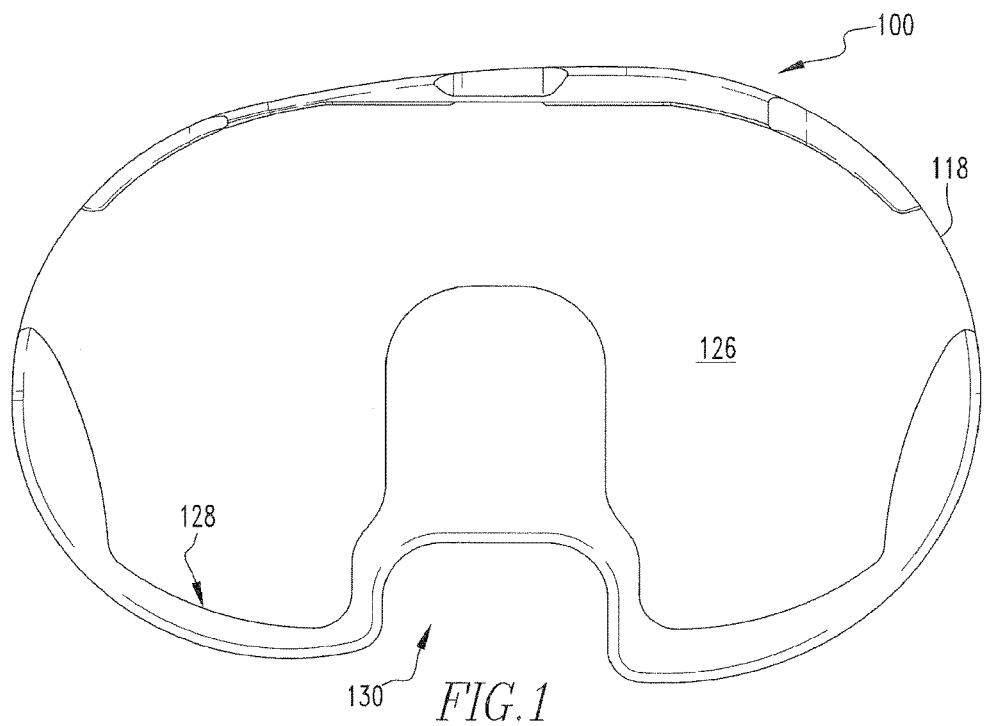
FIG. 1 is a top plan view of one non-limiting example of a tibial tray.
Figure 2:
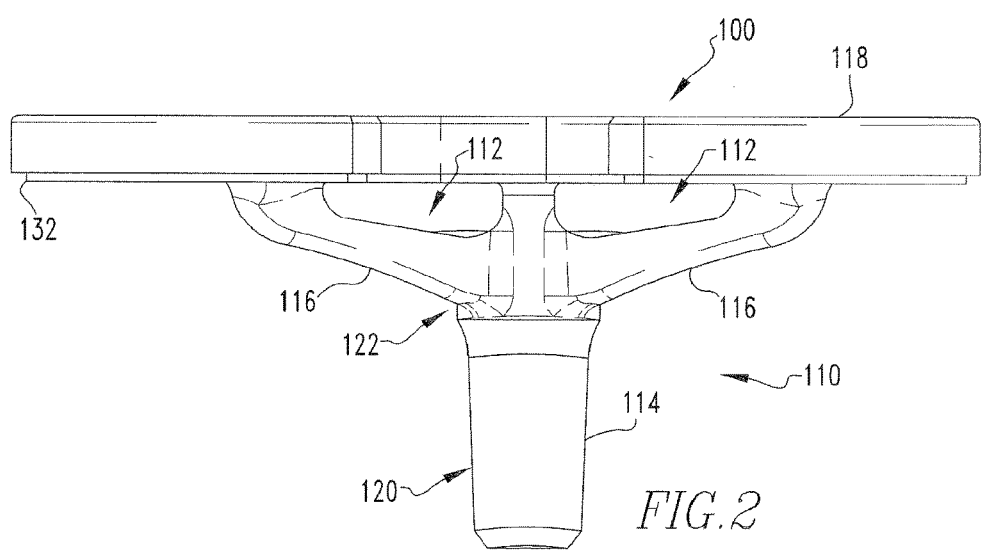
FIG. 2 is a rear elevation view of the tibial tray of FIG. 1.
Figure 3:
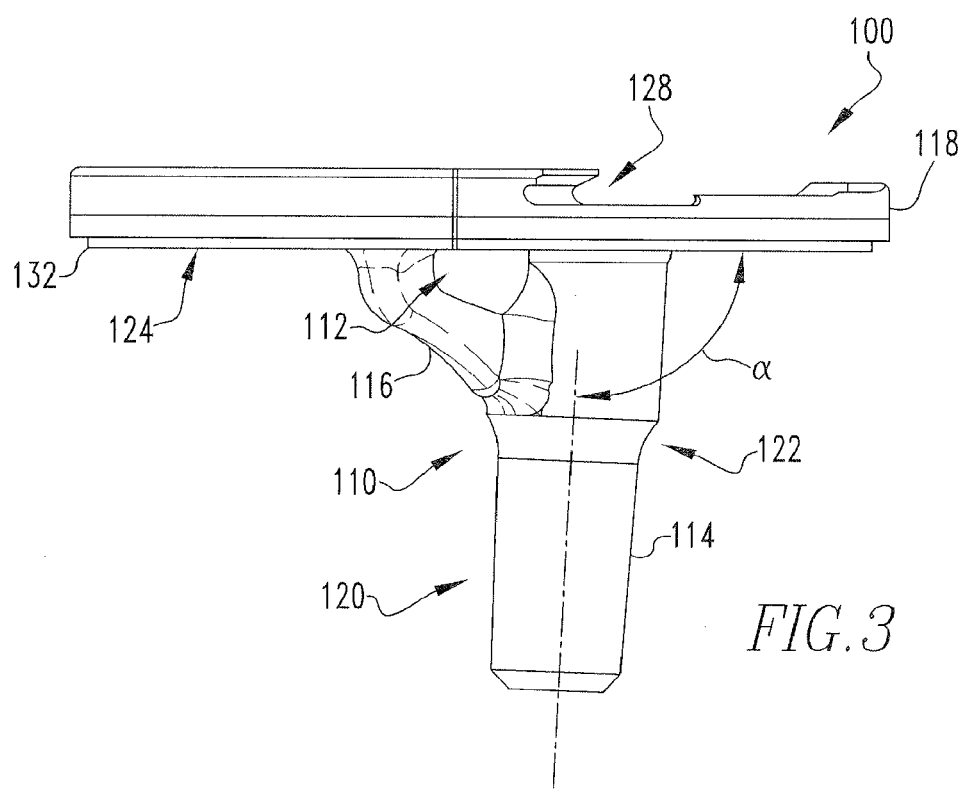
FIG. 3 is a side elevation view of the tibial tray of FIG. 1.

FIGS. 1 through 3 illustrate a non-limiting example of a tibial component 100. As shown in FIGS. 2 and 3, the tibial component 100 includes support member 110 defining a pair of openings 112. In some, although not necessarily all, embodiments, these openings may be sized, positioned, oriented and otherwise constructed to: (1) reduce by a certain degree the stiffness of the implant while maintaining a certain degree of strength; (2) facilitate the visualization (such as through x-ray imaging or other techniques) of lucent lines or other signs that the implant is loosening; (3) facilitate the loosening of the tray from the bony anatomy in the event resection is necessary, such as by facilitating the movement of cutting or other types of instrumentation through and to the far side of the keel/stem portion that would not otherwise be accessible to the cutter or other instrumentation; and/or (4) facilitate bony-ingrowth or otherwise enhance the stability of the implant in the bone. In some embodiments, the openings may not feature all of these benefits or may provide other beneficial features.

The support member 110 shown in FIGS. 2 and 3 includes a stem portion 114 and two arms 116 extending therefrom. In this particular example, the support member 110 is attached to an underside of a tibial tray 118 at three points forming a tripod-like construct. The stem portion 114 shown includes a lower cylindrical portion 120 and an upper portion 122 that is blended to the arms 116. In the depicted embodiment, the stem portion 114 slants at an angle α and in an anterior-posterior direction as it extends away from an inferior surface 124 of the tray 118; however, in other embodiments, the stem portion 114 may have other geometries. The stem portion 114 of this particular tibial component 100 is located anteriorily on the tray 118, although other locations are also possible. The arms 116 shown in FIGS. 2 and 3 extend posteriorly and outwardly from a mid-point of the stem 114 and curve to connect to the underside of the tibial tray 118. In other embodiments, other numbers of arms and/or stems in other configurations and geometries can be employed.

The arms 116 and stem portion 114 of the support member 110 shown in FIGS. 2 and 3 define two openings 112 abutting the inferior surface 124 of the tibial tray 118. In other embodiments, different numbers, configurations, shapes, orientations, and positionings of the openings may be possible. As discussed below, in some embodiments, the openings 112 of the support member 110 may not be "openings" at all in the traditional sense, but may be areas where other materials or components are located, or in which the material forming the tibial component 100 has different properties or characteristics.

In some embodiments, the openings 112 formed in the support member 110 increase certain flexibility characteristics of the tibial component 100 while not overly impinging on a desired strength characteristic of the component. In some embodiments, the openings 112 can be sized and shaped so that the remaining solid material is relatively uniform in shape. In some embodiments, the remaining solid material is uniform in shape in the regions of highest stress at the most peripheral edges of the arms 116. In some embodiments, the opening size can be configured to be short enough to allow a sawblade to easily clear material away from the sides while being tall enough to allow a thin and narrow osteotome to pass through in order to facilitate revision surgery. In other embodiments, the openings 112 may be configured to only permit a sawblade or an osteotome, but not both. In some embodiments, such as, for example, where revisability is not a primary goal, taller and deeper openings may be used to facilitate maximal ingrowth through and around the openings.

In some embodiments, the openings 112 formed in the support member 110 provide for better visualization of the tibial component 100, the bone surrounding the tibial component, and the interface or interfaces between the bone and the tibial component 100. The openings 112, in some embodiments, may act as "windows" facilitating the visualization of lucent lines or other visual indications on the imaging data, which may suggest or indicate that the tibial component is loosening or provide other information for evaluating other issues or concerns. In some embodiments, the size, shape, placement and/or orientation of the openings 112 can be optimized to facilitate visualization of bone-implant interfaces and other areas of interest for future visualization of the implant after installation. For instance, as shown in the Figures, the openings 112 are primarily oriented in a coronal plane, although, in other embodiments, they could be primarily oriented in a sagittal plane or other orientations. In some embodiments, a wider attachment region with a less abrupt thickness change may be used to provide for lower stress in the region. In some embodiments, a more narrow attachment region may be used to increase visibility by lessening the amount of material that could block a user's view.

In some embodiments, the openings 112 are not physical openings extending through the support member 110 or other portion of the tibial component, but may instead be components or areas that do not completely or partially impair visualization such as by x-ray technologies or other visualization technologies. For instance, in some embodiments, the "openings" may be filled or may be comprised of materials of lower density (such as materials for facilitating bony in-growth or other materials) or that are otherwise semi or completely radio-lucent.

Figure 26:
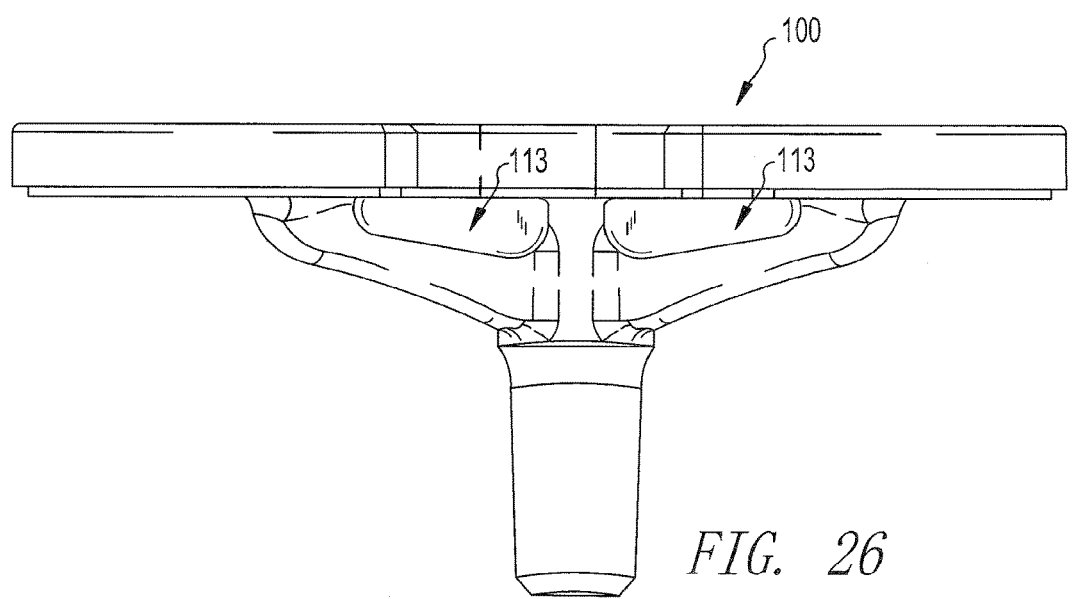
FIG. 26 is a rear elevation view of an alternative embodiment of a tibial tray.

In some embodiments, the openings 112 allow a cutting device or other instrument to physically pass through one or more of the openings 112 to facilitate cutting or otherwise loosening the tibial component from the bone in the event a revision procedure is necessary. In the embodiment shown in FIGS. 2 and 3, the openings 112 are oriented such that posterior-lateral portions of the bone-implant interface can be accessed by a surgical cutter or other instrument if an anterior-medial approach to accessing the joint space is used. The openings 112 shown in FIGS. 2 and 3 also may allow this and other portions of the bone-implant interface to be accessed from other approaches or directions. In other embodiments, the position, orientation, size, shape and number of openings 112 could be altered to facilitate access to remote portions of the bone-implant interface depending on the particular implant involved, the expected surgical approach or approaches that may be utilized, and/or other factors (e.g. the size and shape of the instrument(s) that might need to pass through the opening). Referring to FIG. 26, in some embodiments, the "openings" are not necessarily physical openings through the support member 110 but are areas 113 that are frangible or otherwise capable of being relatively-easily penetrated by a surgical instrument to access the remote portions of the bone-implant interface if necessary. In some embodiments, the opening(s) could be designed to function as guides for the instrumentation passing through them, which, in some uses, might control depth and/or direction of insertion of the instrument (e.g. to lessen chance of damaging surrounding anatomy, such as postero-lateral nerves or arteries) or other aspects of the procedure. In some embodiments, openings 112 can be configured for improved visibility and an ability to approach from anterior to posterior. In some embodiments, the opening(s) 112 could be designed to accommodate surgical cutting instruments such as reciprocating or oscillating planar saw blades having cutting edges on either or both of a distal end or one or both sides, milling bits and other types of rotating cutting devices, chisels, other osteotomes, prying devices, or any other type of surgical instrument that might be used for a revision procedure.

As mentioned above, in some embodiments, the openings 112 could be filled with a porous structure or material or otherwise define in-growth surfaces. In some embodiments, the porous structure or material could be formed from the same material as the rest of the support member 110 but having a different porosity, density or other characteristics than other portions of the support member 110. In some embodiments, the porous structure is not necessarily confined to the opening 112 and could occupy geometric volumes outside of and around other portions of the support member 110. Indeed, in some embodiments, the support member 110 could function as an internal scaffolding for a volume of bone in-growth material(s) that completely or at least in portions encompass the support member 110. In other embodiments, other materials or structures may fill the openings 112 and a porous structure or treatment is not necessary. In some embodiments, the filling material or structure may be intended to facilitate anti-rotation aspects of the implant.

FIG. 1 shows a superior surface 126 of the tibial tray 118, which includes attachment feature 128 for receiving and/or securing one or more articular inserts (not shown) to the tibial tray 118, such inserts designed to contact and articulate with a femoral orthopaedic implant (not shown) in use. In the depicted embodiment, the attachment feature 128 is a shaped channel to receive and lock-in the articular insert. In other embodiments, the tibial tray 118 itself may include articular surfaces and does not require separate articular inserts. The tibial tray 118 shown in FIGS. 1 through 3 includes a posterior notch 130, which may be designed to allow preservation of the attachment site of a posterior cruciate ligament, although, in other embodiments, the tibial tray 118 may or may not include this or other notches or gaps for preserving one or both of the cruciate ligaments. In other words, the tibial tray, in some embodiments, may be for use in a cruciate sacrificing procedure, a posterior cruciate preserving procedure, or a bi-cruciate preserving procedure. In some embodiments, the tibial tray 118 may be used for a mobile bearing knee joint or a fixed bearing knee joint. It will be appreciated that a variety of upper surface and peripheral shapes are possible according to various embodiments and that such shapes can be influenced, at least in part, by strength requirements for the tray. For example, in some embodiments, a cruciate notch or dovetail mechanism may be used, but may also act as a stress-riser.

The tibial component 100 shown in FIGS. 1 through 3 may be part of a set of tibial trays of various standard sizes, or may be a patient-matched tibial tray with certain geometries and/or other aspects of the tray customized for a particular patient's anatomy. The tibial component 100 shown in FIGS. 1 through 3 may be formed from biocompatible materials typically used to manufacture orthopaedic implants or may be formed from other materials. The tibial component 100 shown in FIGS. 1 through 3 may be formed using any desired or appropriate methodologies or technologies.

In some embodiments, the tibial component 100 may be manufactured using Selective Laser Sintered technologies ("SLS") or other free-form fabrication technologies, such as one or more of the EOS Laser-Sintering systems available from EOS GmbH of Munich, Germany. For instance, in some embodiments, the entire tibial component 100 may be formed as a monolithic implant (including any porous or other in-growth promoting surfaces or materials). In other embodiments, portions of the tibial component 100 may be formed using SLS technology and then additional in-growth materials, surfaces, and/or treatments could be added or applied to the implant. In other embodiments, electron beam melting methods or methods that use lasers to subtract or remove select portions of material from an initially solid fin may be used. In other embodiments, portions or all of the tibial component can be formed using casting or other technologies or methods. In some embodiments, a non-porous implant such as a tibial component may be formed using SLS technologies and subsequently that implant may be subjected to acid etching, grit blasting, plasma spraying (e.g. of titanium oxide or another metal to promote in-growth) or other treatments.

FIGS. 4 through 8 illustrate a modular stem 200 that may be used with the tibial component 100 of FIGS. 1 through 3 in some, although not necessarily all, embodiments. Indeed, in some embodiments, the tibial component of FIGS. 1 through 3 will be used without any modular stem or otherwise incorporating any of the features or constructs of the modular stem shown in FIGS. 4 through 8. The modular stem 200 may connect to the stem portion 114 of the support member 110 of the tibial component of FIGS. 1 through 3 via a taper fit mechanism (which may be further secured by a screw or other fastener in some embodiments). In other embodiments, other mechanical attachment mechanisms may be employed, or, in still other embodiments, the stem is not modular but an integral part of the tibial component.

The embodiment of the modular stem 200 shown in FIGS. 4 through 8 includes an inner core 210 from which a plurality of flutes 212 extend. In some embodiments, the inner core 210 has a tapered, conical or press fit geometry positioned and oriented for where it is most likely (at least in some cases) to encounter "harder" bone, and the flutes 212 are positioned where they are most likely to encounter "softer" bone. In some embodiments the general shape of the modular stem 200 facilitates implantation in a relatively close orientation and position to a pre-defined orientation and position.

Figure 6:
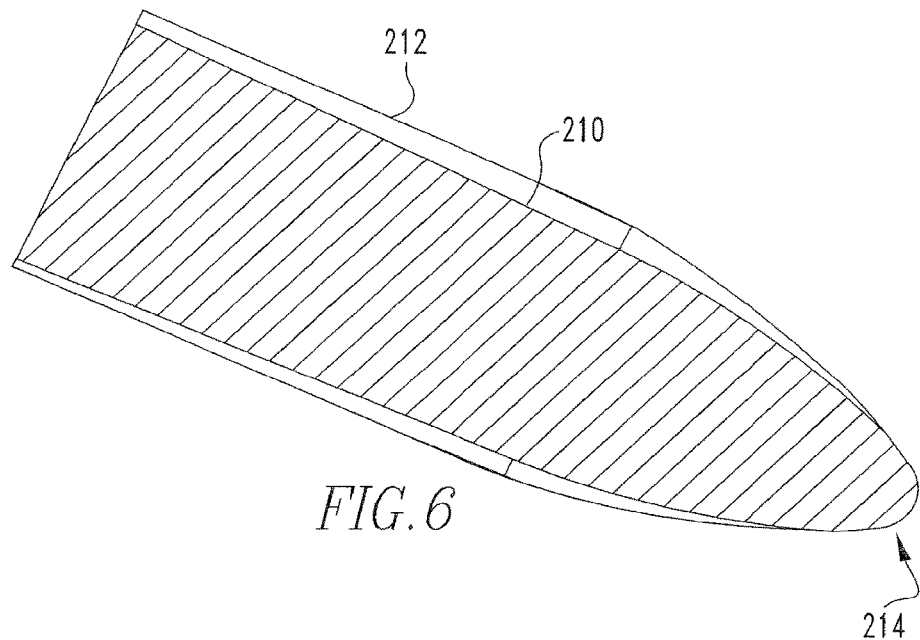
FIG. 6 is a cross-section of the stem of FIG. 4 taken along line 6-6 shown in FIG. 5.

As shown in FIG. 6, the inner core 210, in some embodiments, may be slightly tapered and/or define a somewhat conical shape. Conical features such as this one (whose axes, at least in some embodiments, may be directed generally parallel to the direction of load application) may be beneficial because, in some uses, they may convert what otherwise would be a purely compressive load into a compressive load that also has a transverse component (i.e. a direction of which could be characterized, at least in some embodiments, as orthogonal to the direction of the compressive load). In some embodiments, this may be beneficial in preventing bone immediately adjacent to the implant from being shielded from loading, at least for some of the time. In some cases, bone that is shielded from loading could remodel, resorb or otherwise degrade, resulting in a poor quality bone-implant interface. The tapered or conical shape of the modular stem 200 may also facilitate the prevention of subsidence or migration. The tapered or conical nature of the inner core 210 may also facilitate a press-fit type interface between the implant and bone. In the embodiment shown, a distal tip 214 of the inner core is rounded.

Figure 4:
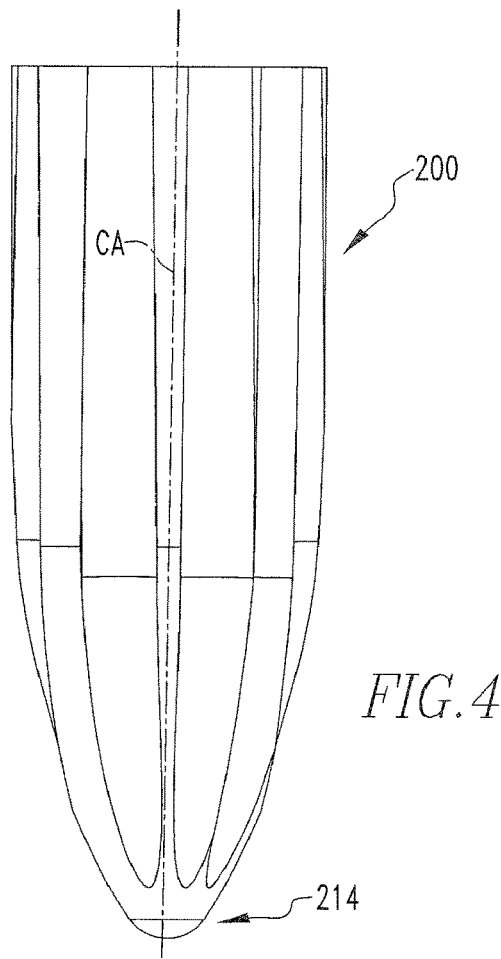
FIG. 4 illustrates a modular stem that may optionally be used with the tibial tray of FIG. 1.
Figure 5:
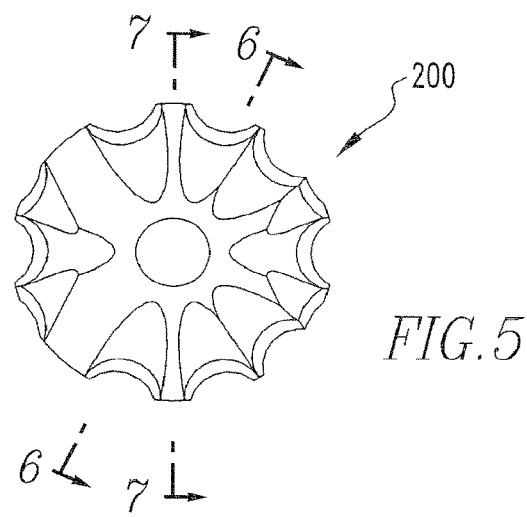
FIG. 5 is a distal view of the modular stem of FIG. 4.
Figure 7:
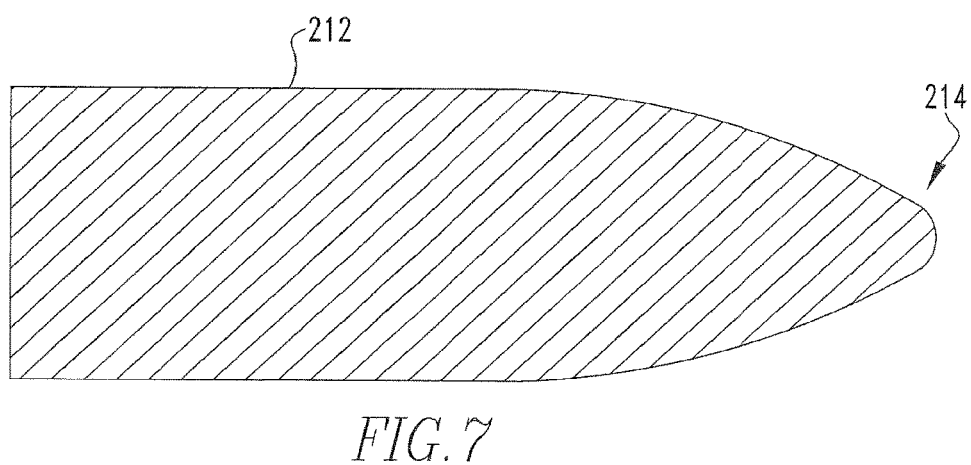
FIG. 7 is a cross-section of the stem of FIG. 4 taken along line 7-7 shown in FIG. 5.

As shown in FIGS. 4, 5, and 7, several flutes 212 extend radially from the inner core 210 of the modular stem 200. In the particular embodiment shown, the flutes 212 extend in a radially symmetric pattern such that the apexes of the flutes 212 are parallel to a central axis CA of the inner core 210. In other words, although the inner core tapers, the apexes of the flutes extend along a virtual cylinder. In other embodiments, the apexes of the flutes may also taper as they extend towards the distal tip of the stem; although, in at least some of these embodiments, the flutes do not taper as much as the inner core. Because, at least in some embodiments, the inner core tapers to a greater degree than the apex of the flutes, the flutes will "protrude" from the stem to a greater extent at distal portions of the stem than at proximal portions of the stem. Accordingly, in some embodiments, such a design may pose less of a risk of fracturing the hard bone that is located proximate the proximal portions of the stem while still achieving fixation (rotational and/or translational) in the soft bone located proximate the distal portions of the stem. Additionally, in some embodiments, there may be less of a risk of deflection or mal-orientation or mal-position due to lack of or lessening of press-fit between the flutes and the hard bone.

Figure 8:
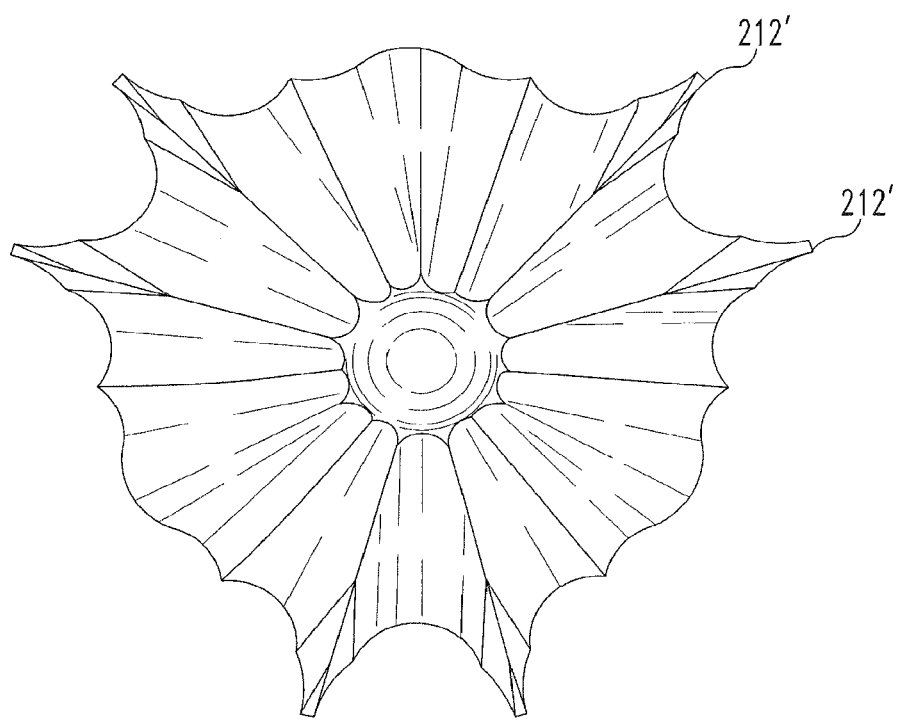
FIG. 8 illustrates a distal view of an alternative embodiment of fluting useable with a modular stem such as the modular stem of FIG. 4.

As shown best in FIG. 8, in addition to the flutes 212 described in the previous paragraph, the inner core of the modular stem may also include secondary/smaller fluting 212' extending therefrom. In some embodiments, the secondary fluting 212' may be rounded or sharp, and may further facilitate a tight fit with the surrounding bone, while, because they are smaller, lessening the chance of tibial pain. In some embodiments, the fluting is radially symmetric and facilitates insertion of the stem 200 to follow a pilot hole. FIG. 8 shows fluting useable in some embodiments of modular stems in which the stem 200 has fluting (or at least primary fluting) that is spaced 120 degrees apart.

In some embodiments, the fluting is not radially symmetrical, but instead exhibits planar symmetry. Planar symmetry may allow, in some embodiments, matching of the fluting to the support member geometry of a tibial component. In some embodiments, the fluting is not radially symmetrical and is instead "handed" and specific for left or right tibias to accommodate particular or expected locations of hard and soft bone. In some embodiments, patient matched technologies could be employed to customize the fluting to the hard vs. soft bone distribution of the specific patient.

In some embodiments, the fluting may be tapered. In some embodiments, the "soft bone flutes" may be designed in such a way that over small sections, they may be lower than the "hard" bone flutes. In some embodiments, the "soft" bone flutes could be parallel to the "hard" bone flutes but become tangentially wider to increase their effectiveness in soft bone. In some embodiments, the flutes could be discontinuous. In some embodiments, the flutes could be made of a material different than that of the rest of the stem. In some embodiments, portions of the stem could be porous coated or have surface finishes applied.

Figure 9:
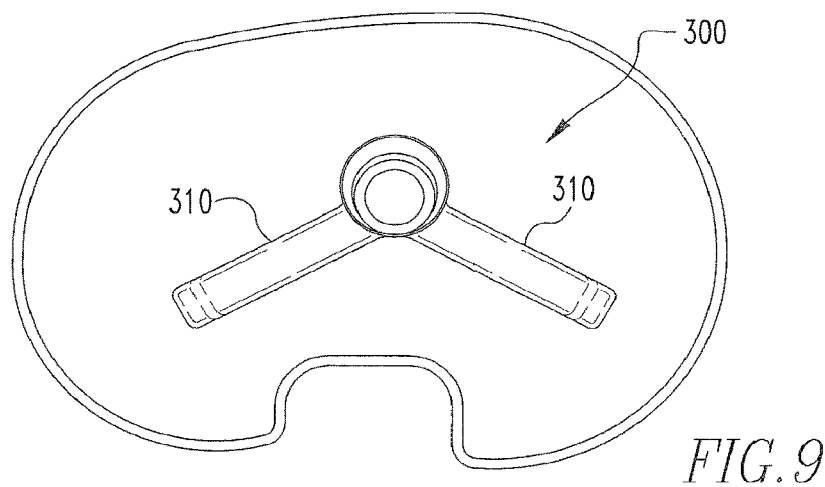
FIGS. 9-14 illustrate schematically an alternative embodiment of a tibial tray with a modular stem.
Figure 10:
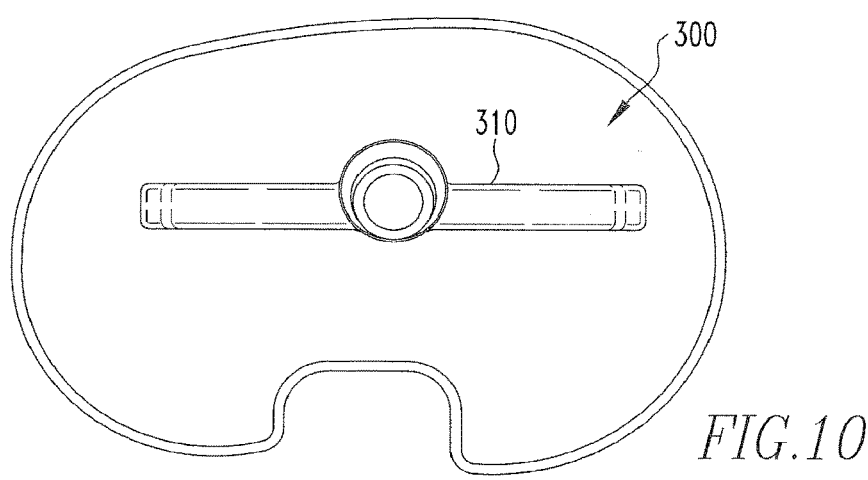
Figure 11:
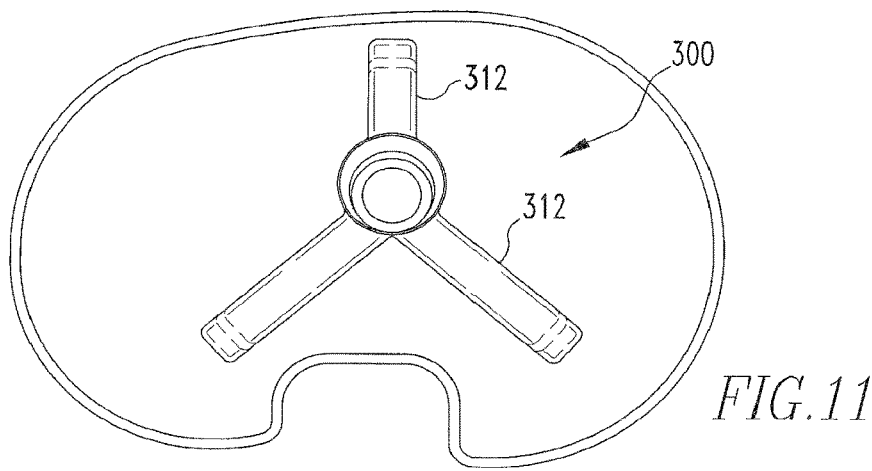
Figure 12:
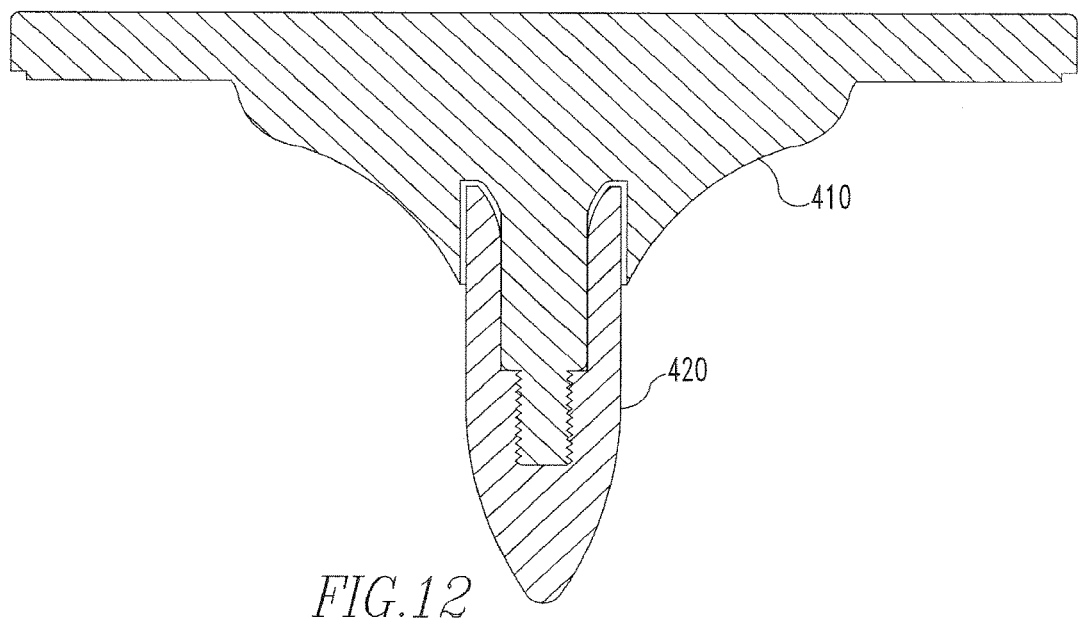

FIGS. 9-11 illustrate alternative possible support member shapes. For example, in FIGS. 9 and 10, there are two branches 310 (or arms or wings) of the support member 300. In FIG. 9, the branches 310 are angled relative to one another, but in FIG. 10 the branches 310 are substantially aligned with one another. In FIGS. 11 and 12, the support member 300 has three branches or arms 312. Fewer or greater numbers of branches are possible.

Figure 13:
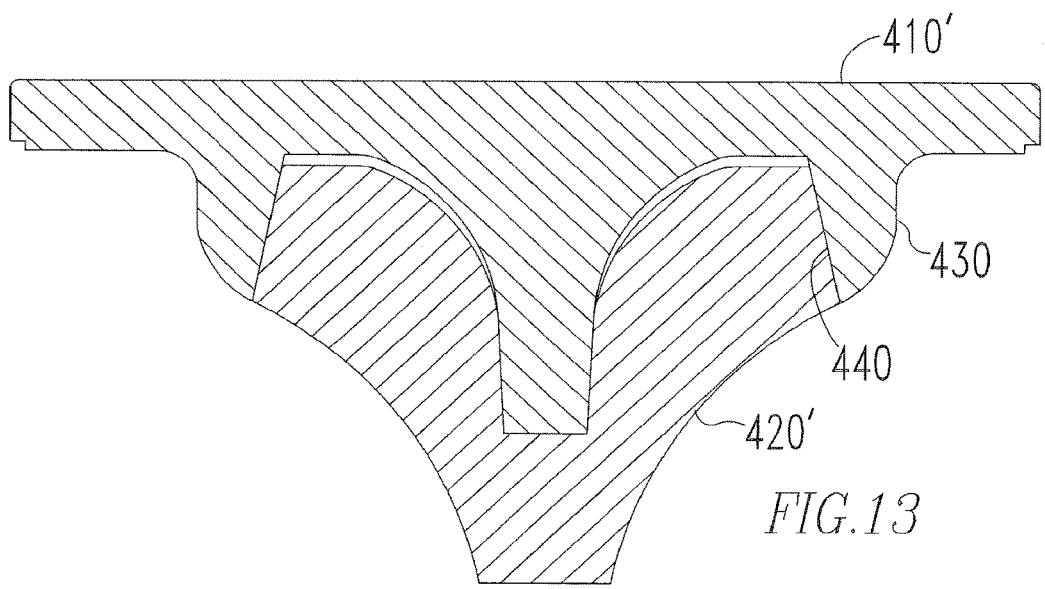
Figure 14:
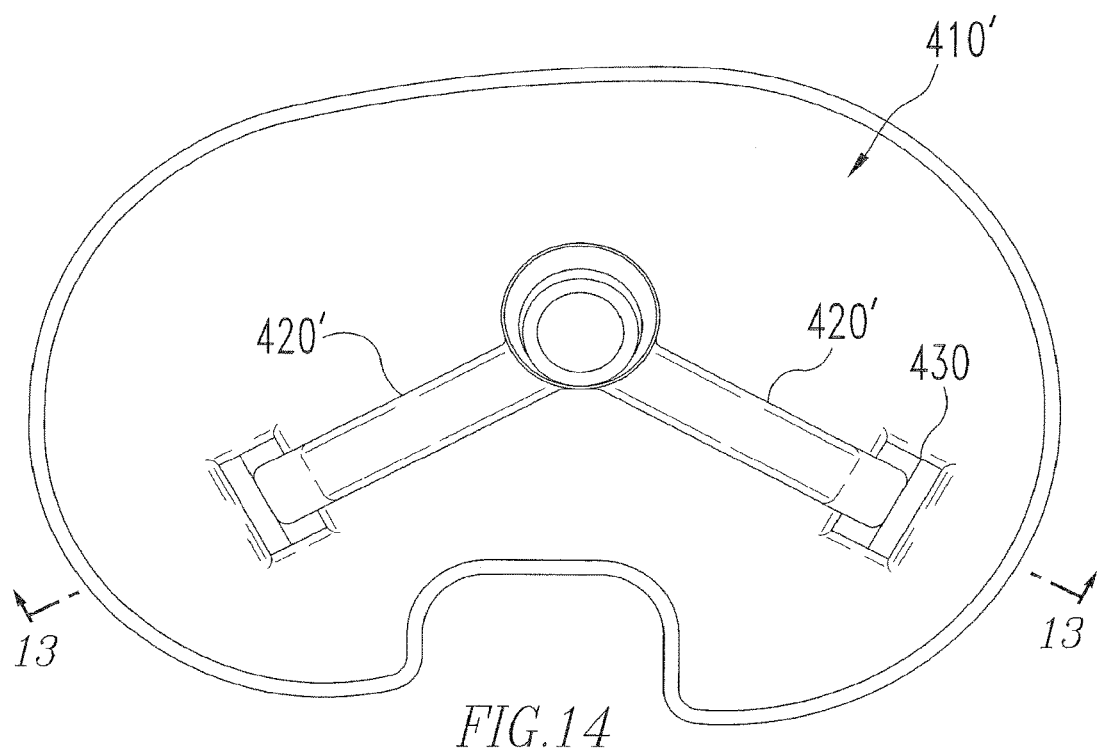

As illustrated in FIGS. 12, 13 and 14, the tibial tray 410 and support member 420 may be modular and may have a male/female arrangement. Although in the figures the stem portion 420 is shown to have a female portion and the tibial tray 410 is shown to have a male portion, these could be reversed. In the embodiment depicted in FIG. 13, the tibial tray 410' has a shoulder 430 that engages a ledge 440 of the stem portion 420'. The shoulder/ledge arrangement allows force to be transferred from the tibial tray 410' to the stem portion 420'. The shoulder/ledge arrangement also provides clearance or a gap between the tibial tray 410' and the stem portion 420' which may be used for visualization and/or as a guide in revision surgery. Further, the area between the tibial tray 410' and the stem portion 420' may be used by a surgeon to separate the components in revision surgery. The shoulder 430 also may provide a porous surface area for bone in-growth. As best seen in FIG. 13, the stem portion 420' may engage in a taper lock with a portion of the tibial tray 410'.

Figure 15:
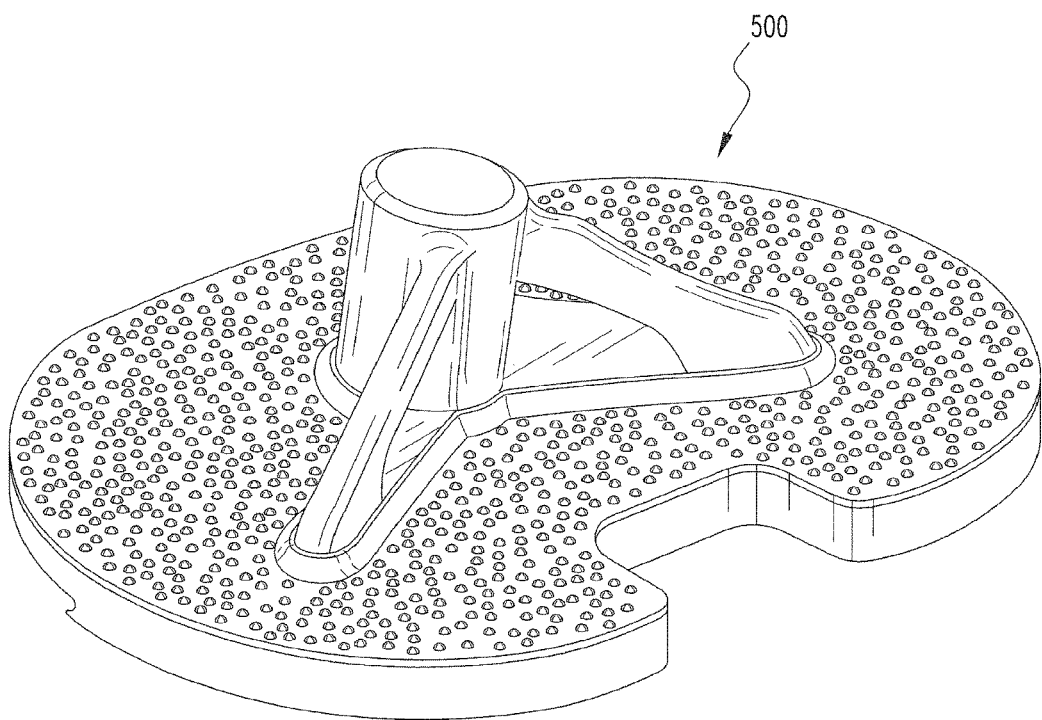
FIG. 15 illustrates a further embodiment having porous beaded coatings.

FIG. 15 shows one embodiment of a tibial component 500 having a porous bead coating. The porous bead coating mimics the bumpy outer surface geometries and profiles of clinically-successful porous beads, with the roughness and porosity of a desired trabecular substrate. The porous bead coating may be applied to one or more of the following: the inferior surface of the tibial tray, the support member, the stem portion, the arms, the modular stem, or the modular stem flutes. Other locations are possible.

Figure 16:
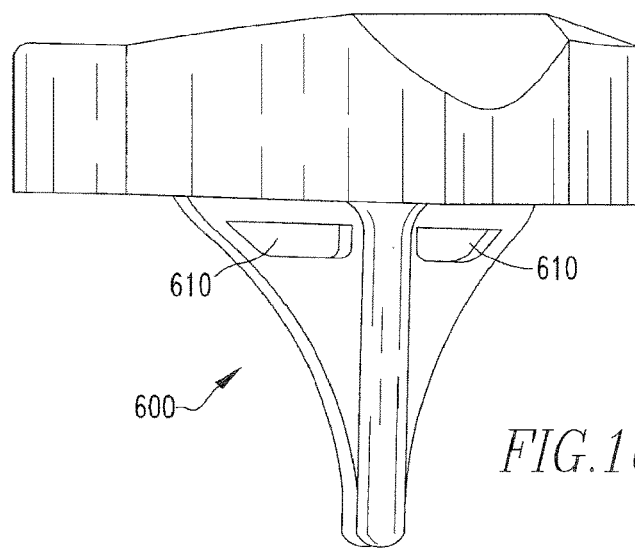
FIG. 16-19 illustrate alternative embodiments having various stem configurations.
Figure 17:
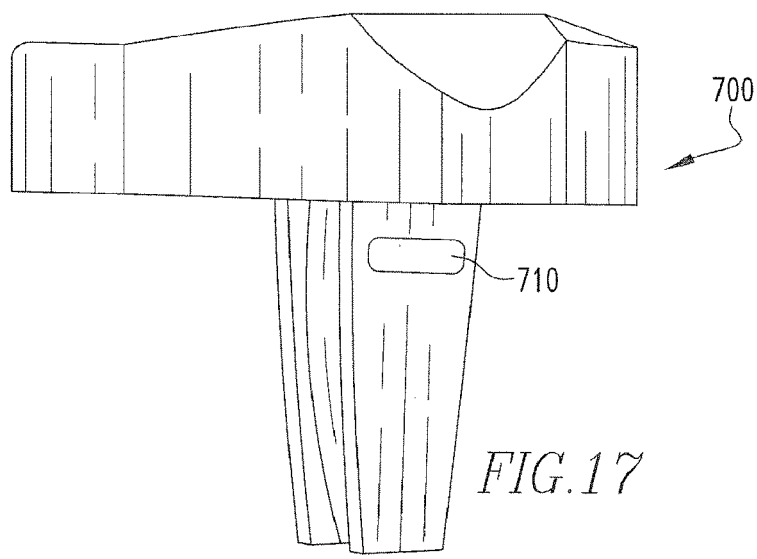
Figure 18:
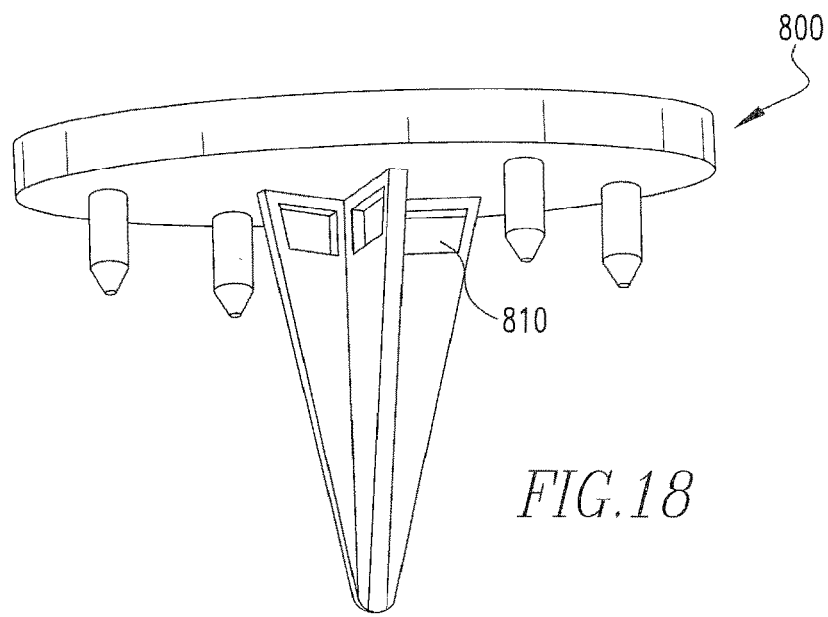
Figure 19:
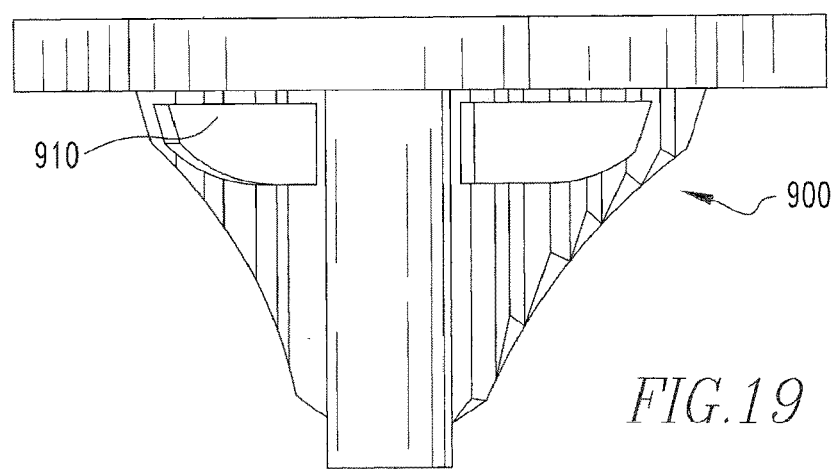

FIGS. 16-19 illustrate possible alternative embodiments of the support member. In FIG. 16, there is a support member 600 having openings or windows 610. The support member 600 has a "wing-like," two-sided "vane" shape with arcuate longitudinal sides. FIG. 17 illustrates a support member 700 with opening 710. The support member 700 has a general "I-beam" shape. FIG. 18 illustrates a support member 800 with openings 810. The support member has a four-sided "vane" shape with linear longitudinal sides. In FIG. 19, there is a support member 900 having openings or windows 910. The support member 900 has a corrugated "wing-like," two-sided "vane" shape with compound arcuate longitudinal sides. Of course, other variations are possible.

Referring now to FIGS. 20-25, further embodiments to provide components having porous beaded coatings and methods for their manufacture. Because implants and natural bone usually have different degrees of flexibility, uneven stress distributions may occur. Consequently, when an implant is loaded, there is generally some relative movement at the interface between the bone (more compliant) and the implant (more rigid). Many implants thus employ an intermediate material such as bone cement to reduce the amount of relative movement; however, cementless implants may rely on relative roughness to achieve the same goals.

Historically, small spherical beads, bundles of thin wires, and thermal-sprayed metal have been used to produce the friction necessary to reduce the amount of relative movement. Optionally, screws and/or press-fit features may improve the fixation of implant to bone. Such technologies are generally accepted by the orthopedic surgeon community. However, the geometric nature of these coatings limits the location and size of their porosity. Newer technologies, such as those that employ asymmetric beads or metallic foams have improved the location and size of porosity, but they are difficult to manufacture with favorable surface textures. Remedies have included placing hatch lines into the surface of an already porous coating (e.g., via machining). Other porous surfaces have been manufactured having sharp protrusions at a microscopic level. These protrusions can cause problems when there is even a small amount of relative movement between the bone and implant. The sharper protrusions can dig into the bone and create bone particles or can break off from the implant and create wear particles at the implant-bone interface. In addition to loosening the attachment between the implant and bone, these loose particles can cause harmful complications.

The shortcomings of previous porous surfaces are addressed by providing an implant having a surface that is textured with numerous blunt protrusions on a macroscopic level and has a porous structure on a microscopic level. The blunt protrusions create friction that reduces the amount of relative movement between an implanted component and surrounding bone. The porosity allows the surrounding bone to grow into the implant, and the lack of relative movement between implant and bone facilitates this ingrowth.

A consideration in designing and creating a porous implant having blunt protrusions is the size and density of the protrusions. The protrusions create an area on which the bone initially contacts an implant. If the protrusions are too large or spaced too far apart, the majority of the implant's surface area between the protrusions will be too far from the bone for the bone to grow into the implant, and the bone may be unable to create a solid interface with the implant. In contrast, if the protrusions are too small or located too close together, their effect will be minimal and an implant may encounter the same problems as prior implants with smoother surfaces or surfaces composed of many concentrated sharp protrusions. An ideal surface contains protrusions that are large enough to create the needed friction between the bone and implant and still small enough to still allow for a high degree of bone ingrowth into the porous surface. The protrusions may be any suitable height, and preferably are between about 50 µm and about 2000 µm. For certain applications, it may be preferable to limit the protrusion heights to between 200 µm and 400 µm to achieve the desired level of friction and ingrowth with surrounding bone.

Protrusions on a surface of an implantable component may be any suitable shape or profile desired for a general or specific application of the component. In certain embodiments, each surface protrusion may be a bump shaped as a portion of a sphere above the surface of the implant. Protrusions may also be shaped like wires or any other suitable features, including features common to cementless implants.

Figure 20:
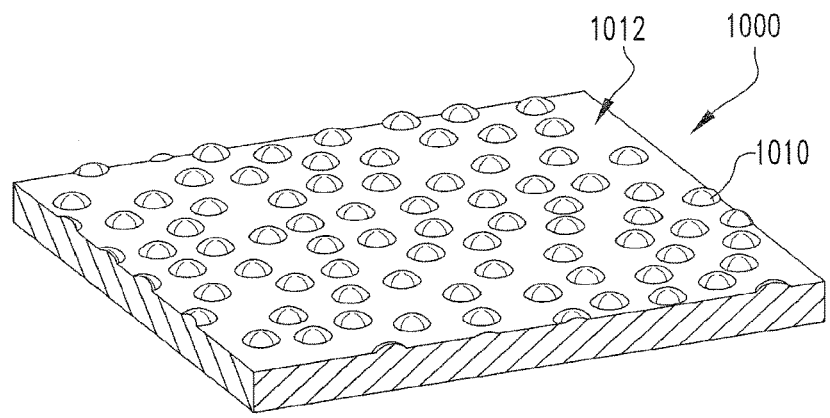
FIG. 20-25 illustrate further embodiments to provide components having porous beaded coatings and methods for their manufacture.

Referring now to FIG. 20, an orthopaedic implant 1000 has a porous surface that mimics the bumpy outer surface geometries and profiles of clinically-successful porous beads, with the roughness and porosity of a desired ingrowth interface. The surface of implant 1000 is textured by blunt protrusions 1010, which are shaped substantially as hemispherical bumps. The protrusions 1010 are sized and spaced to create desirable friction that reduces movement of the implant 1000 relative to surrounding bone while allowing the surrounding bone to grow substantially into the porous protrusions 1010 and porous surface area 1012 between the protrusions. In addition to the protrusion heights discussed above, the spacing and density of protrusions 1010 affect the amount of friction and bone ingrowth created. Any suitable density of protrusions 1010 may be used for an implant, and the protrusions preferably occupy between about 10% and about 60% of the surface. The protrusions may be concentrated to a density of between about 0.25 beads/mm$^2$ and about 6 beads/mm$^2$.

Improved implants, such as the implant 1000 of FIG. 20, may be formed by any suitable approach, and may be formed using one of the following four methods.

A first method includes the steps of: 1) providing a mold having a negative impression of a porous beaded surface, 2) providing an implant substrate, which may be solid or porous, to be coated, 3) interposing small asymmetric particles between the implant substrate and said mold, and 4) applying a pressure and/or an elevated temperature to the mold, implant substrate, and small asymmetric particles to create a "green-state" implant (i.e., ready for full sintering) or a final implant (sintered), the implant having a roughened porous coating with an outer surface geometries and profiles mimicking a clinically-proven porous beaded structure with the roughness and porosity of a desired trabecular structure.

A second method includes the steps of: 1) creating a 3D model simulating an outer surface profile of a porous beaded implant, 2) creating a model of an implant substrate volume, 3) applying the 3D model simulating an outer surface profile of a porous beaded implant to the 3D model of the implant substrate volume to create a bumpy pre-form volume, 4) applying an algorithm to fill the bumpy pre-form volume with a desired interconnected porous or otherwise reticulated structure to create a porous implant model, and 5) creating an implant having a roughened porous texture with an outer surface profile geometry mimicking a clinically-proven porous beaded structure using the implant model in a rapid-manufacturing process.

A third method includes the steps of: 1) providing a mold of an implant having an inner surface mimicking a negative image of an outer surface profile geometry of a porous beaded surface, 2) providing a plurality of small asymmetric particles, 3) placing the plurality of small asymmetric particles into the mold, and 4) applying a pressure and/or an elevated temperature to the mold and/or small asymmetric particles to create a "green-state" implant (i.e., ready for full sintering) or a final implant (sintered), the implant having a roughened porous texture with an outer surface profile geometry mimicking a clinically-proven porous beaded structure.

A fourth method includes the creation of a beaded surface on a foam component during the precursor step of making a metallic foam, the method comprising the steps of: 1) providing a mold of an implant having an inner surface mimicking a negative image of an outer surface profile geometry of a porous beaded surface, 2) loading one or more foaming agents into the mold, 3) creating a porous foam component (e.g., polymeric, polyurethane) in the general shape and/or size of said implant, which has an outer surface geometry mimicking an outer surface profile geometry of a porous beaded surface, 4) removing the porous foam component from the mold, 5) applying a binder or binding agent to the porous foam component, 6) applying a plurality of small symmetric or asymmetric particles (or a combination thereof) to the porous foam component having a binder or binding agent thereon, 7) subjecting the porous foam component having binder or binding agent and particles thereon to an elevated temperature to sinter the particles together and/or burn out the foam component to form a "green-state" implant (i.e., ready for full sintering) or a final implant (sintered), the implant having a roughened porous texture with an outer surface profile geometry mimicking a clinically-proven porous beaded structure. Implant has a bumpy outer surface profile and geometries mimicking a clinically-proven porous-beaded structure.

The substrate forming at least an outer portion of the implant may be a bulk porous, reticulated structure resembling a trabecular structure. One or more core portions or outer surface portions of the implant may be solid (e.g., a portion of the implant may be configured for articulation with another implant component). The implant may also include one or more solid internal portions. For example, implant 1000 shown in FIG. 20 may include a solid structural portion on the interior of the implant. The structural portion may be a single solid area or multiple solid areas on the interior of implant 1000 that provide a series of structural ribs to add support to the implant. The solid internal structure may have any suitable shape and configuration, such as a structural lattice similar to rebar in concrete. Illustrative but non-limiting examples areas where the internal structure may be desired include areas around screw holes, the equator region of an augment, or any other suitable area. In some embodiments, a polymer foam could be melted or burned to have the shape of beads—or the foam could be polymerized on a bead-shaped subsurface resulting in the end-product having a bead-shaped surface.

For rapid-manufacturing technologies, the bead surface geometries and profile could be created virtually and subtracted out from a bulk porous entity or virtual beads could be created and combined with a porous entity. It is the general intent, in some, but not necessarily all, embodiments that the end-product be homogenous. Alternate embodiments of implants may include surface profiles that mimic metallic wire bundles or the peaks and valleys of a thermal sprayed coating. Once a virtual model of the desired geometry is created using modeling software, an implant component having the desired surface profile can be created using any suitable rapid manufacturing techniques. For example, the porous implant can be created using 3D printing technology that uses powdered metal to "print" the modeled implant. In such an approach, a foam may be created having a surface profile that includes protrusions, such as protrusions 1010 in FIG. 20, and the profiled foam may then be filled in with powdered metal to create a porous microstructure with the profiled surface. A foam that does not contain the protrusions may also be used to create the porous microstructure with powdered metal, and the desired surface profile with protrusions can then be stamped into the surface of the porous metal implant.

Advantages of implants manufactured this way are that they contain integral porosity with the initially bone-engaging surface profile of clinically-proven porous beads. In other words, the same features providing the traction needed between bone and implant are the same features providing a surface for bone to grow into and around for a rigid and enduring fixation surface. As non-limiting examples, Tables A and B show some examples of potentially suitable bead density (spacing), and diameter.

TABLE A

Chart of number of beads in selected area and average and standard deviation of bead diameter of 50 beads on a shell used with the Birmingham Hip ® Resurfacing system available from Smith & Nephew, Inc. in at least 3 fields of view (SEM, Jeol, Japan)

| Beads in 6.4 × 4.8 mm area | Bead Diamter (mm) | |
|---|---|---|
| 11 | Average D | 1.24 |
| 20 | Std D | 0.12 |
| 20 | | |

TABLE B

Percent solid for typical beaded product for bone ingrowth.

| Product | Company | Implant Type | Percent Solid |
|---|---|---|---|
| CoCr ROUGHCOAT (2-layer) | Smith and Nephew | Profix ® Femoral | 46.3% |
| CoCr Porocoat (3-layer) | DePuy | LCS ® Knee Femoral | 46.5% |
| CoCr Porocoat (3-layer) | DePuy | AML ® Stem | 50.2% |
| Ti ROUGHCOAT (2-layer) | Smith and Nephew | Synergy ™ Stem | 51.9% |

Wherein, "percent solid" is a 2D measurement of bead density produced by typical metallographic techniques based on the test method disclosed in ASTM F1854, entitled "Standard Test Method for Stereological Evaluation of Porous Coatings on Medical Implants," which is incorporated by reference herein in its entirety.

Figure 21:
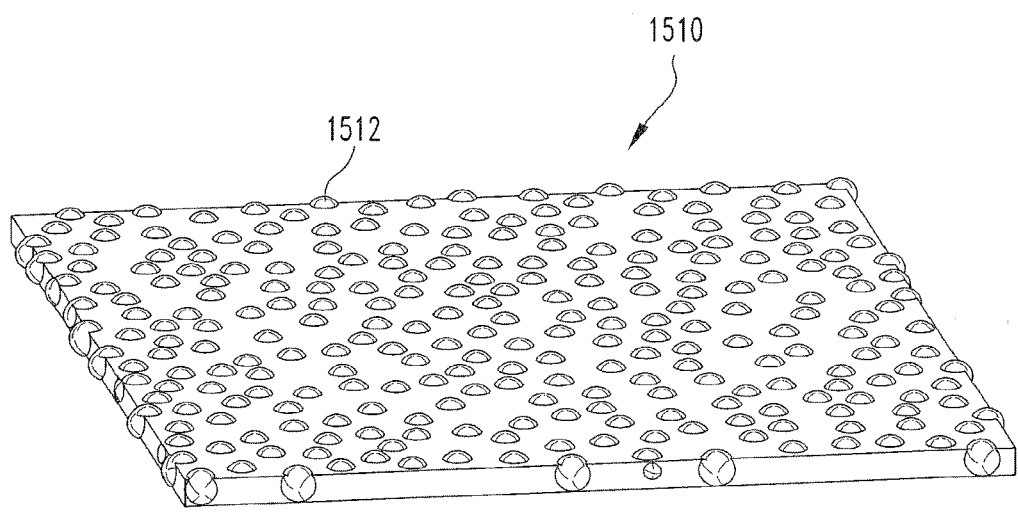

FIG. 21 shows a coating volume 1510 having spherical bead volumes 1512 placed therein, such that the spherical bead volumes 1512 protrude from the coating volume 1510 to form a second coating volume mimicking a spherical bead profile. Alternatively, solid spherical beads may be combined into a porous coating. To create the coating volume 1510, two software models can be created and then merged to form the final model of the porous volume with the profiled protrusion surface. A first model of a macroscopic structure of the volume, including the plurality of bead volumes 1512, can be created in modeling software, and may look substantially the same as the volume shown in FIG. 21.

Figure 22A:
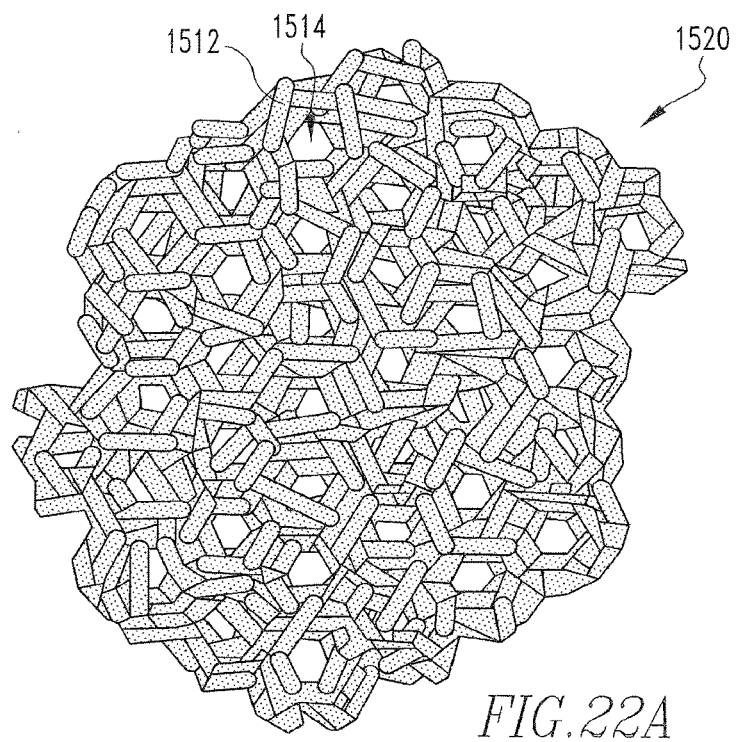
Figure 22B:
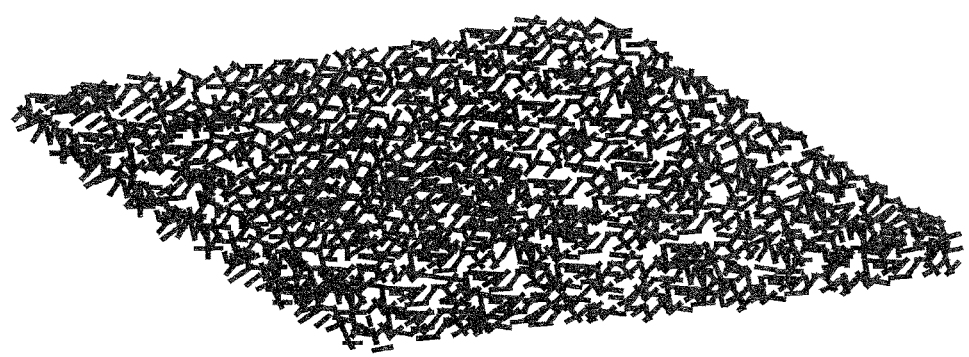

A second software model can be created to produce the porous microscopic structure desired for a macroscopic volume, such as the volume shown in FIG. 21. FIG. 22A shows a unit cell 1520 of an exemplary porous reticulated structure, which may configured to fill the coating volume mimicking a spherical bead profile. The unit cell 1520 is made up of a complex structure of struts 1512. The arrangement of struts 1512 creates voids 1514 within unit cell 1520, thus making the desired porous microstructure. The size and arrangement of struts 1512 can be varied to control the number and size of voids 1514. By controlling the size and arrangement of the struts 1512, a desired amount and profile of the porous structure is achieved. FIG. 22B schematically illustrates a conglomeration of unit cells on a macroscopic level.

Figure 23:
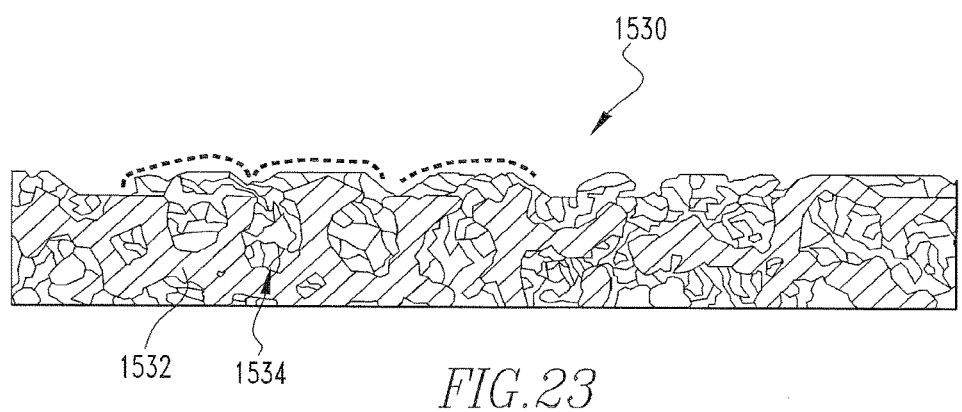

FIG. 23 shows a cross section of a coating volume 1530, which may correspond to coating volume 1510 of FIG. 21, mimicking a spherical bead profile after the volume has been replaced with a reticulated structure (e.g., via a repeating unit cell such as unit cell 1520 in FIG. 22A in CAS software, or using any of the 4 methods described above). The finished coating volume 1530 exhibits both the profiled macrostructure and porous microstructure. The dotted lines in FIG. 23 outline the surface profile of coating volume 1530 and show the protrusions that create a bumpy surface that produces friction with bone when implanted. The microstructure of coating volume 1530, made up of a combination of solid structure 1532 and voids 1534, creates a porous implant into which surrounding bone can grow to fill in voids 1534 and create a solid mating of implant and bone.

Figure 24:
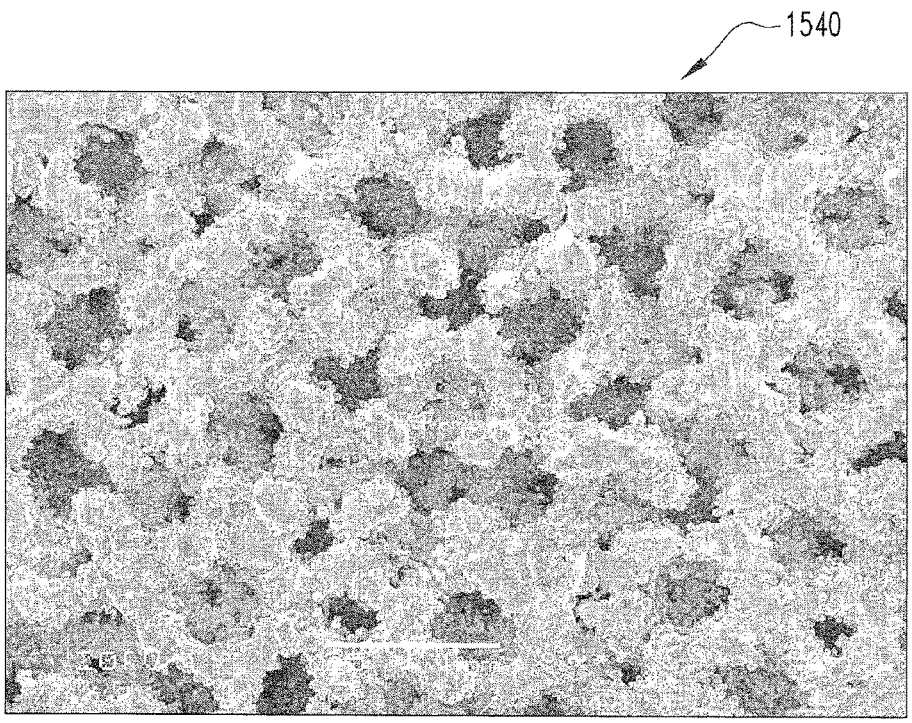
Figure 25:
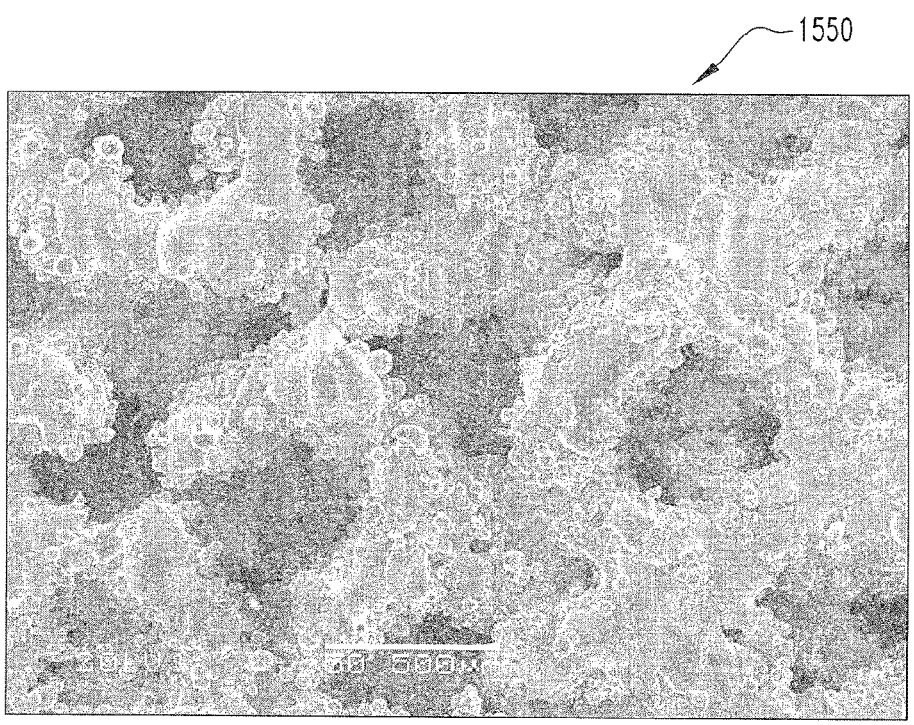

FIG. 24 shows an SEM image 1540 taken at 25× magnification of the surface of a part made by the disclosed method. Surface topography is not apparent with this view. FIG. 25 is an SEM image taken 1550 at 50× magnification of the structure made with the disclosed method. The structures shown in FIGS. 24 and 25 exhibit the porous microstructure discussed above with respect to coating volumes 1510 and 1530, and can be created by merging a solid macrostructure with a porous microstructure model, such as the unit cell 1520 in FIG. 22A.

As a further non-limiting example, the following chart shows some additional exemplary parameters that have proven to be useful for various embodiments. In the chart below, MVIL refers to Mean Void Intercept Length, which is another way of characterizing the average pore size, particularly in structures where the pore shapes and sizes are not uniform. On generally known definition of MVIL is "measurement grid lines are oriented parallel to the substrate interface. The number of times the lines intercept voids is used with the volume percent void to calculate the mean void intercept length."

|  | Electron beam melting (EBM) | Direct metal laser sintering (SLS) Eurocoating EOS | Landon Structure (FIG 4) |
|---|---|---|---|
| Avg. Strut Thickness (μm) | — | 275-450 (360) | 275-400 (340) |
| Avg. Pore Size: MVIL | 300-920* (565) | 450-690 (560) | — |
| Average Pore Window Size: (μm) | 900-1300* | 1310 ± 280 | 1970 ± 40 |
|  | — | 370 ± 100 | 830 ± 150 |
|  | Not Specified 670-1340 | 600 ± 100 | — |

*(fine, medium, and coarse structures)

It is generally desirable to provide between about 60-85% porosity. Pore sizes may generally range between about 50-1000 microns. In the above example, the smallest pore size provided was about 300 microns, and the smallest window was about 595 microns across at its largest diameter. It will be understood that this example is intended to be non-limiting and provided for illustrative purposes only.

The systems, methods, and devices described herein to create implants having both a profiled macrostructure and a porous microstructure can allow a medical professional to utilize customizable, patient-specific implants. A customized implant can be efficiently created using the rapid manufacturing techniques discussed herein by merging two or more models of an implant and then printing the modeled component. This could allow a medical professional, such as an orthopedic surgeon, to order an implant specific to a single patient, including modeling the size and shape of the implant to fit defects or other unique features of the patient's anatomy. This process can also be automated by taking bone scans of the patient's anatomy or using other available medical imaging and modeling techniques to automatically create a 3D model to use for rapid manufacturing.

The ability to customize an individual implant also allows a medical professional to adjust the detailed macrostructure and microstructure of the implant to fit the needs of a particular application. For example, an orthopedic surgeon can adjust the macrostructure of the implant by selecting the shape, height, density, or other characteristics of protrusions on the surface of the implant. The surgeon can also customize the number and size of voids within the implant to achieve a desired porosity for the implant. In some embodiments, the surgeon may also select the configuration of the macrostructure of the implant. For implants that include internal solid portions for strength and structure, the surgeon can customize the size and location of the internal solid portions to provide the structure in certain non-uniform areas of the implant where increased strength is needed. Illustrative but non-limiting examples areas where increased strength may be desired include areas around screw holes, the equator region of an augment, connection sites of augments, augment areas that are thinner than others, or any other suitable area. The surface profile of the implant can also be non-uniform if different areas of the implant require different levels of friction or surface area for a bone interface. A surgeon may want a higher concentration of surface protrusions in certain areas of the implant, such as areas that experience higher levels of stress, and a lower concentration of protrusions, or no protrusions at all, in other areas.

Porous implants described herein allow for an implant to provide a good contact surface area and friction regardless of the quality of bone into which an implant is implanted. For example, patients who have soft spongy bone may need features that are longer, and a lower number of those features. Patients with hard dense bone may require features that are shorter, but a higher number of those features to create the same fixation in the bone. The specific requirements of a patient's anatomy and bone quality can be accommodated by the individualized design options provided by the porous implants described herein.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A tibial component comprising:
   a tibial tray with a superior side and a planar inferior side;
   a support member extending from the planar inferior side of the tibial tray, the support member having a stem portion that slants at an angle relative to the planar inferior side of the tibial tray in an anterior-posterior direction, the support member further including at least two arms that are angled relative to one another, each of the arms defining an opening;
   wherein the tibial tray and the support member are monolithic;
   wherein a portion of each of the openings is defined by the stem portion; and wherein the at least two arms extend posteriorly and outwardly from a mid-point of the stem portion, and the at least two arms curve to connect to the inferior side of the tibial tray to form the openings.

2. The tibial component according to claim 1, further comprising a porous bead coating.

3. The tibial component according to claim 1, the inferior side further comprising a porous coating.

4. The tibial component according to claim 1, wherein the openings are located adjacent the inferior side of the tibial tray.

5. The tibial component according to claim 1, wherein the openings are spaced apart from the inferior side of the tibial tray.

6. The tibial component according to claim 1, wherein the stem portion comprises an upper portion that is blended to the at least two arms.

7. The tibial component according to claim 1, wherein the stem portion comprises a fluted portion.

8. The tibial component of claim 1, wherein the openings are comprised of solid, frangible material.

9. The tibial component of claim 1, wherein the planar inferior side has a planar surface with a porous beaded coating, the planar surface with the porous beaded coating extending outward from the keel to an anterior, posterior, medial, and lateral periphery of the planar inferior side.

10. A tibial component comprising:
a tibial tray with a superior side and a planar inferior side;
a support member extending from the planar inferior side of the tibial tray, the support member comprising:
a stem portion that slants at an angle relative to the planar inferior side of the tibial tray in an anterior-posterior direction, wherein the stem portion is located anteriorly on the tibial tray, the stem portion has a proximal end and a distal end, and the proximal end is connected to the planar inferior side of the tibial tray; and
at least two arms that are angled relative to one another, each of the arms defining an opening, wherein the openings are located adjacent the planar inferior side of the tibial tray and are spaced apart, the at least two arms extend posteriorly and outwardly from a mid-point of the stem portion, and the at least two arms curve to connect to the planar inferior side of the tibial tray to form the openings;
wherein the stem portion comprises an upper portion that is blended to the at least two arms; and wherein a portion of each of the openings is defined by the stem portion.

11. A tibial component comprising:
a tibial tray with a superior side and a planar inferior side; and
a support member extending from the planar inferior side of the tibial tray, the tibial tray and the support member are monolithic, the support member comprising:
a stem portion that slants at an angle relative to the planar inferior side of the tibial tray in an anterior-posterior direction, wherein the stem portion is located anteriorly on the tibial tray, the stem portion has a proximal end and a distal end, and the proximal end is connected to the planar inferior side of the tibial tray;
at least two arms that are angled relative to one another, each of the arms defining an opening, wherein the openings are located adjacent the planar inferior side of the tibial tray and are spaced apart, the at least two arms extend posteriorly and outwardly from a mid-point of the stem portion, and the at least two arms curve to connect to the planar inferior side of the tibial tray to form the openings;
wherein the stem portion comprises an upper portion that is blended to the at least two arms and
wherein a portion of each of the openings is defined by the stem portion.

* * * * *